United States Patent [19]

de Macario et al.

[11] Patent Number: 4,682,891
[45] Date of Patent: Jul. 28, 1987

[54] MICROCIRCLE SYSTEM

[75] Inventors: Everly C. de Macario, Delmar; Robert J. Jovell, Albany; Alberto J. L. Macario, Delmar, all of N.Y.

[73] Assignee: Health Research, Incorporated, Albany, N.Y.

[21] Appl. No.: 775,582

[22] Filed: Sep. 13, 1985

Related U.S. Application Data

[63] Continuation-in-part of Ser. No. 739,969, May 31, 1985.

[51] Int. Cl.[4] .......................... G01N 21/03; C12M 1/20
[52] U.S. Cl. .................................... 356/244; 356/246; 422/102; 435/301
[58] Field of Search ................ 250/576; 356/244, 246, 356/440; 435/299, 300, 301; 422/102

[56] References Cited

U.S. PATENT DOCUMENTS

| | | | |
|---|---|---|---|
| 2,561,339 | 7/1951 | Chediak | 435/300 |
| 3,415,361 | 12/1968 | Adams, Jr. et al. | 435/299 |
| 3,736,042 | 5/1973 | Markovits et al. | 356/246 |
| 3,992,265 | 11/1976 | Hansen | 435/300 |
| 4,299,920 | 11/1981 | Peters | 435/299 |
| 4,319,841 | 3/1982 | Suovaniemi et al. | 356/246 |

FOREIGN PATENT DOCUMENTS

| | | | |
|---|---|---|---|
| 0146143 | 6/1985 | European Pat. Off. | 435/299 |
| 3336738 | 5/1985 | Fed. Rep. of Germany | 435/300 |
| WO84/02775 | 7/1984 | PCT Int'l Appl. | 356/246 |

Primary Examiner—F. L. Evans
Attorney, Agent, or Firm—Curtis, Morris & Safford

[57] ABSTRACT

A microcircle system designed to replace a conventional microtitration plate of the type having a plurality of microwells. A generally rectangular base formed of a frame of height ad length substantially equal to the height and length, respectively, of the conventional microtitration plate. The width of the frame is no greater than the width of the conventional microtitration plate; and in one embodiment, the width is equal to a submultiple of the width of the conventional microtitration plate. A pair of support ledges extends towards the interior of the frame from opposite sides thereof, these ledges serving to support at least one tile which is formed as a thin sheet of material having an array of retaining elements that retain drops of liquid samples.

31 Claims, 10 Drawing Figures

MICROCIRCLE SYSTEM

This a continuation-in-part of U.S. patent application Ser. No. 739,969, filed May 31, 1985.

BACKGROUND OF THE INVENTION

This invention relates to apparatus for retaining small drops of liquid samples, for purposes of analysis and, more particularly, to such apparatus that is designed to replace conventional microtitration plates of the type having plural microwells, which plates normally are used in a conventional microtitration plate support provided in, for example, microplate readers, sample-loaders, and the like.

The chemical and biological analyses of various liquid samples have been facilitated by equipment which now has become conventional. Such equipment includes spectrophotometric systems that are manually or automatically operated to provide spectroanalysis of such liquid samples, and loading apparatus for introducing those samples into microwells. These systems are commercially available from, for example, Bio-Tek Instruments Inc. of Burlington, Vt., Models EL307, EL308 and EL310 microplate readers; Bio-Rad Laboratories, Model 2550 EIA microtitration plate reader; Dynatech Laboratories, Inc. of Alexandria, Va., Models Mini Reader II, Micro Fluor and microsample loading apparatus Models Dynadrop SR, Autopipetter and Rotatiter. The aforementioned equipment cooperates with microtitration plates which, generally, are of plastic material, are of generally rectangular configuration and are integrally formed with an array of so-called microwells, each storing a liquid sample for analysis.

Such microtitration plates are useful in measuring the presence, type and quantity of, for example, biological and biochemical entities. Conventional microtitration plates typically are used in the measurement of specific proteins, such as antigens, antibodies, enzymes, hormones, etc. Such microtitration plates have an array of microwells, such as 96 microwells arranged in an 8×12 array, each microwell being loaded with a liquid sample on the order of about 100–200 microliters ($\mu$l) of sample or reagent. The sample contained in one of more of such microwells is analyzed by the relative positioning of that microwell with respect to, for example, the reading head of the aforementioned readers. Samples in successive or selected ones of such microwells may be analyzed in rapid order.

However, although such conventional microtitration plates are used widely in several applications, and although several reading and sample-loading devices compatible with such microtitration plates are available, various disadvantages and drawbacks are associated with such microtitration plates. For example, the quantity of liquid sample that must be contained by each microwell (on the order of about 200 $\mu$l) is sufficiently large that, in some instances, the total quantity of sample that is available for analysis may be inadequate for satisfactory use with such microwells. Also, the time required to perform each analysis including loading the requisite number of microwells with liquid sample prior to analysis thereof, and the time needed to empty and test-wash such microwells is quite high. This significant delay is a key factor in the overall time needed to analyze such liquid samples and a serious drawback in the use of conventional microtitration plates.

Another disadvantage associated with conventional microtitration plates is the need for large storage space to accommodate a sufficient supply of the relatively large microtitration plates. Also, the ability to utilize only a small portion of the microtitration plate for successive analyses is possible but cumbersome. The present invention has resolved these problems.

Yet another disadvantage attending conventional microtitration plates is the difficulty in observing, for example, by simple light microscopy any biological particulate substance that may or may not be adhering to the walls of a microwell. Since such walls generally are disposed non-perpendicular to the light path of a conventional microscope, particles that might adhere thereto are not easily seen because the path of the light beam generally does not impinge upon such walls. Furthermore, particles adhering to the well bottom cannot be examined with a microscope having powerful objectives, since the objectives cannot be positioned sufficiently close to the bottom of the well because of interference from the walls. Also, it often is difficult to deposit a non-reacting "control" in a microwell with the intention of monitoring that control.

Still another disadvantage found in the use of conventional microtitration plates resides in the need to introduce freshly prepared reagents into the microwells for analysis. It has heretofore generally been difficult, if not impractical, to store previously prepared, dry reagents in such microwells for subsequent activation by the introduction therein of water or water-containing samples for reaction therewith.

OBJECTS OF THE INVENTION

Therefore, it is an object of the present invention to provide apparatus which can be substituted for conventional microtitration plates for compatible use with equipment that has been designed for receiving such microtitration plates.

Another object of this invention is to provide a microcircle system comprised of tiles and a base which, in combination, provides an advantageous substitute for conventional microtitration plates.

A further object of this invention is to provide a tile which, with a base therefor, can be used in place of conventional microtitration plates, the tile having an array of retaining elements which replace the conventional array of microwells and which require only a fraction of the liquid sample (e.g. on the order of 5–10 $\mu$l) previously required by such microwells.

An additional object of this invention is to provide a tile and base therefor as a substitute for conventional microtitration plates and which overcome the aforenoted disadvantages associated with such microtitration plates.

Yet another object of this invention is to provide a base for use with one or more tiles, each tile being replaceable such that one tile may be used with samples of a particular type while others may be used with liquid samples of different types, thereby facilitating the use of variable numbers of samples in various sequences during the course of an assay.

Still an additional object of this invention is to provide a tile that is used with a base, the tile having an array of retaining elements in which dry reagents may be anchored to such retaining elements for subsequent activation by the introduction therein of liquid samples for reaction therewith.

A still further object of this invention is to provide a tile for use with a base, the tile being provided with an array of retaining elements in the form of, for example, thin flat dishes, each of which is capable of anchoring a biological substance thereto for analysis by, for example, a conventional microtitration plate reader.

Still another object of this invention is to provide a base and tile which, in combination, are easier and faster to load, analyze and wash than heretofore had been possible for conventional microtitration plates.

Various other objects, advantages and features of the present invention will become readily apparent from the ensuing detailed description, and the novel features will be particularly pointed out in the appended claims.

SUMMARY OF THE INVENTION

In accordance with this invention, apparatus is provided for use in a conventional microtitration plate support in place of a microtitration plate of the type having a plurality of microwells. A generally rectangular base including a frame of height and length substantially equal to the height and length, respectively, of the conventional microtitration plate is provided with a width that is substantially no greater than the width of that conventional microtitration plate. In one embodiment, the width of the frame is substantially equal to the width of the conventional microtitration plate. In other embodiments, the width of the frame is substantially equal to a submultiple of the width of the conventional microtitration plate. The frame is provided with a pair of support ledges which extend toward the interior of the frame, preferably from opposite sides thereof, these ledges supporting at least one tile which is formed as a thin sheet of material having an array of retaining elements for retaining drops of liquid samples. Preferably, the retaining elements are in the form of thin flat dishes.

In one embodiment, a plurality of substantially identical tiles are supported on the ledges of the frame, each tile being individually removable such that the samples and/or reagents to be analyzed may be easily and quickly modified or changed merely by replacing one of the tiles for another, without requiring all of the tiles to be replaced. To facilitate the ready removal of a tile from the frame, one or more finger slots are disposed in the frame adjacent a supported tile. Preferably, one such finger slot is provided for each tile supported in the frame.

In accordance with another embodiment, the frame is comprised of two frame sections disposable one atop the other, the total height of the frame sections when so disposed being substantially equal to the height of the conventional microtitration plate. In this embodiment, at least one tile is supportable in each frame section. When the frame sections are disposed atop each other, the tile supported in one is spaced from the tile supported in the other, resulting in a liquid bridge formed of a drop of liquid sample being suspended between the retaining elements of the respective tiles. Preferably, the two frame sections are hingedly connected to each other so as to pivot about that hinged connection into and out of overlying relationship.

Preferably, the tile is provided with a water-repellant coating on the surface thereof with the array of retaining elements being substantially free of that coating.

In one use of the tile, one or more dry reagents are anchored to the retaining elements for subsequent activation by the introduction thereinto of liquid samples which react with those reagents. Biological substances that adhere to the retaining elements may be easily analyzed by, for example, a conventional microtitration plate reader.

In the embodiment wherein a plurality of tiles is supported on the frame, the tiles are positioned side-by-side with each other and, preferably, suitable separating means are disposed on the ledges for separating adjacent tiles. Such separating means may comprise upstanding projections from those ledges.

BRIEF DESCRIPTION OF THE DRAWINGS

The following detailed description, given by way of example and not intended to limit the present invention solely to the specific embodiments illustrated herein, will best be understood in conjunction with the accompanying drawings in which.

DETAILED DESCRIPTION OF CERTAIN PREFERRED EMBODIMENTS

Figure 1:
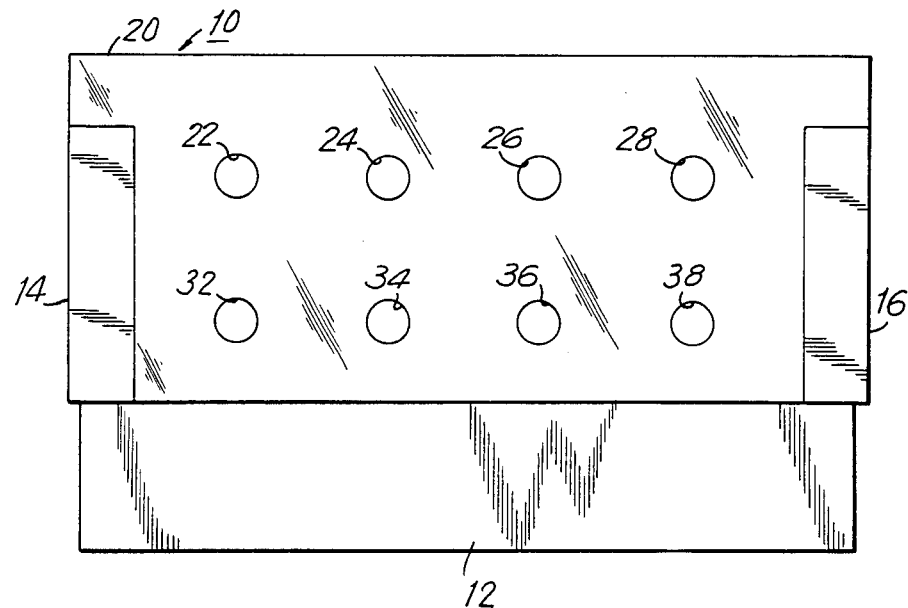
FIG. 1 is a front view of a microsample holder and carrier of the type described in copending application Ser. No. 739,969.

In previously filed application Ser. No. 739,969, a microsample holder and carrier are described for use in conventional horizontal beam spectrophotometers in place of convention cuvettes and cuvette supports. FIG. 1 of the accompanying drawings is a front view of that microsample holder and carrier. As shown in FIG. 1, carrier 10 is comprised of a generally rectangular base 12 having a pair of arms 14 and 16 extending upwardly from a top wall 18 of the base. Preferably, base 12 and arms 14, 16 are formed of one-piece unitary construction of, for example, metal, plastic or other materials normally used to construct conventional cuvette supports. The length, height and width of the carrier are equal to the length, height and width of conventional cuvette supports and, thus, the external dimensions of carrier 10 are substantially identical to the external dimensions of the conventional cuvette support.

Carrier 10 is adapted to carry a microsample holder 20 that is formed as a generally rectangular plate and that is suitably positioned within guide slots (not shown) formed in at least the inner wall of arms 14 and 16. Such guide slots function to position and properly align plate 20 which is easily inserted from above carrier 10 and removed therefrom.

Plate 20 is formed with two sets of retaining elements, such as one row of four retaining elements 22, 24, 26 and 28 and another, aligned row of retaining elements 32, 34, 36 and 38. These retaining elements all are of circular shape having diameters on the order of about 3 mm, each retaining element being capable of retaining a 5–10 $\mu$l sample of liquid to be analyzed. The surfaces of plate 20 other than the circular areas may be coated with a thin layer of hydrophobic material to assure retention of the liquid samples within the circular areas. Each circular sample-retaining area may be formed as a relatively thin flat dish. Reagents or biologicals may be pre-anchored to the circular surfaces of such dishes so that, when liquid samples are applied, the samples come into contact with pre-anchored reagents or biologicals, resulting in onboard, uninterrupted reactions. Thus, plate 20 may be prepared with reactants in advance of use, to await the application of small sample drops to the thus-prepared retaining elements.

Figure 2:
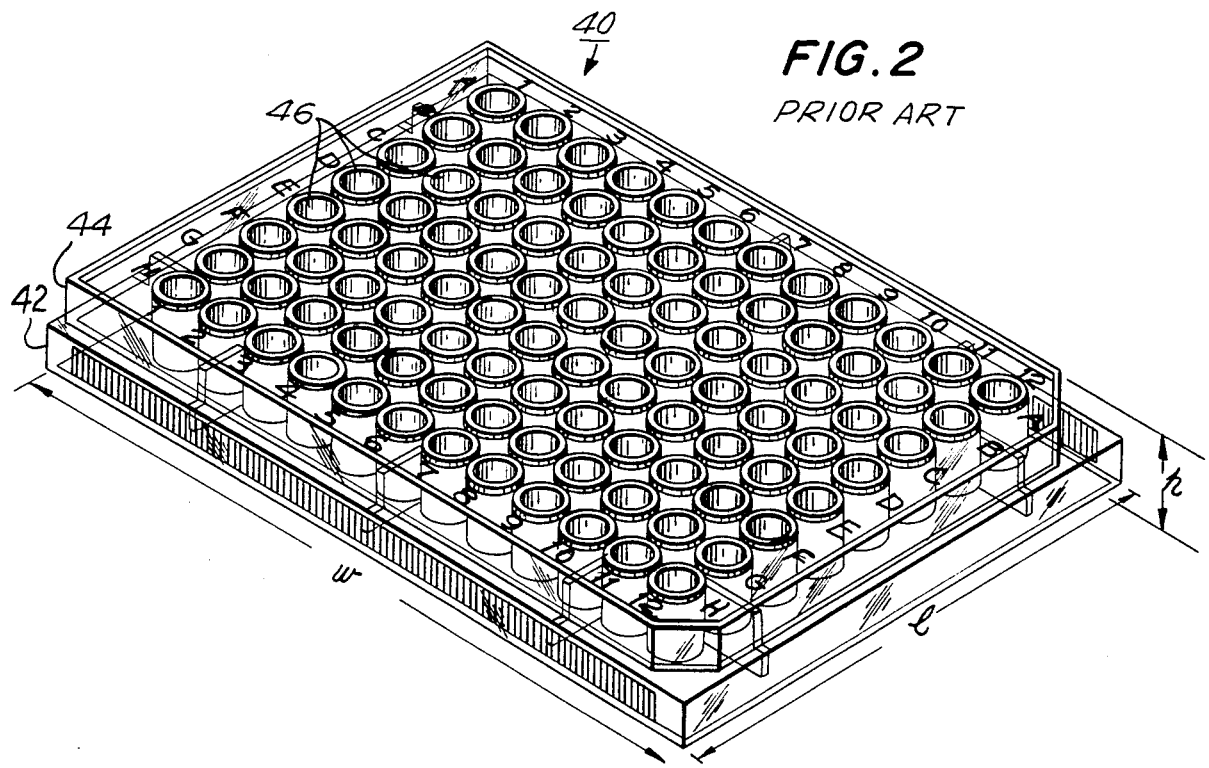
FIG. 2 is a perspective view of a conventional microtitration plate that the present invention can replace with a significant improvement.

Before proceeding with a detailed description of the tile and base of the present invention, a brief explanation of a conventional microtitration plate is provided in conjunction with the perspective view thereof shown in FIG. 2. Conventional microtitration plate 40 is comprised of a generally rectangular stage 42 which supports a holder 44 in which an array of microwells 46 is disposed. The overall dimensions of microtitration plate 40 are seen to be a length l, a width w and an overall height h from the bottom of stage 42 to the common upper surface of microwells 46. Typically, 96 microwells are provided in holder 44, these microwells being disposed in an 8×12 array.

The microtitration plate illustrated in FIG. 2 typically is used with a reader of the type mentioned in the beginning portion of the instant specification. The reader serves to analyze liquid samples contained in respective ones of the microwells for measuring the presence of specific biological and biochemical entities, such as particular proteins or the like. Each microwell has a capacity on the order of about 200 μl; and in some instances, the amount of liquid sample to be measured might not be available in sufficient quantity to fill a microwell. Rinsing of the microwells during the operation of the test procedure is often necessary to remove therefrom all free remnants of the liquid sample that had been previously added. This rinsing procedure is quite time-consuming and difficult.

The microtitration plate shown in FIG. 2 has been found to be less than satisfactory in observing or analyzing biological substances attached to the bottom and vertical walls of microwells 46. Although such substances may be observed under low magnification if they adhere to the floor of the microwell, the fact that the walls of the microwells extend in a direction substantially parallel to the light beam of the conventional microscope tends to prevent effective observation of the biological particles on the walls of the microwells. If attached to the planar well-bottom, biologic particles still cannot be examined under high magnification since the walls of the well do not permit the microscope objective to be positioned sufficiently close to the particles to obtain proper focus.

Notwithstanding the aforementioned drawbacks and disadvantages, apparatus has been developed and now is commercially available for use with microtitration plate 40. For example, microtitration plate supports for use with readers, sample-loaders and the like have been developed for use with standardized microtitration plates having dimensions l, w and h, as illustrated in FIG. 2. The present invention provides an alternative system exhibiting the same overall dimensions l, w and h as the conventional microtitration plate for use with the microtitration plate support that normally is used with microtitration plate 40. Thus, the present invention is compatible with conventional microtitration plate readers, sample-loaders, and the like.

Figure 3A:
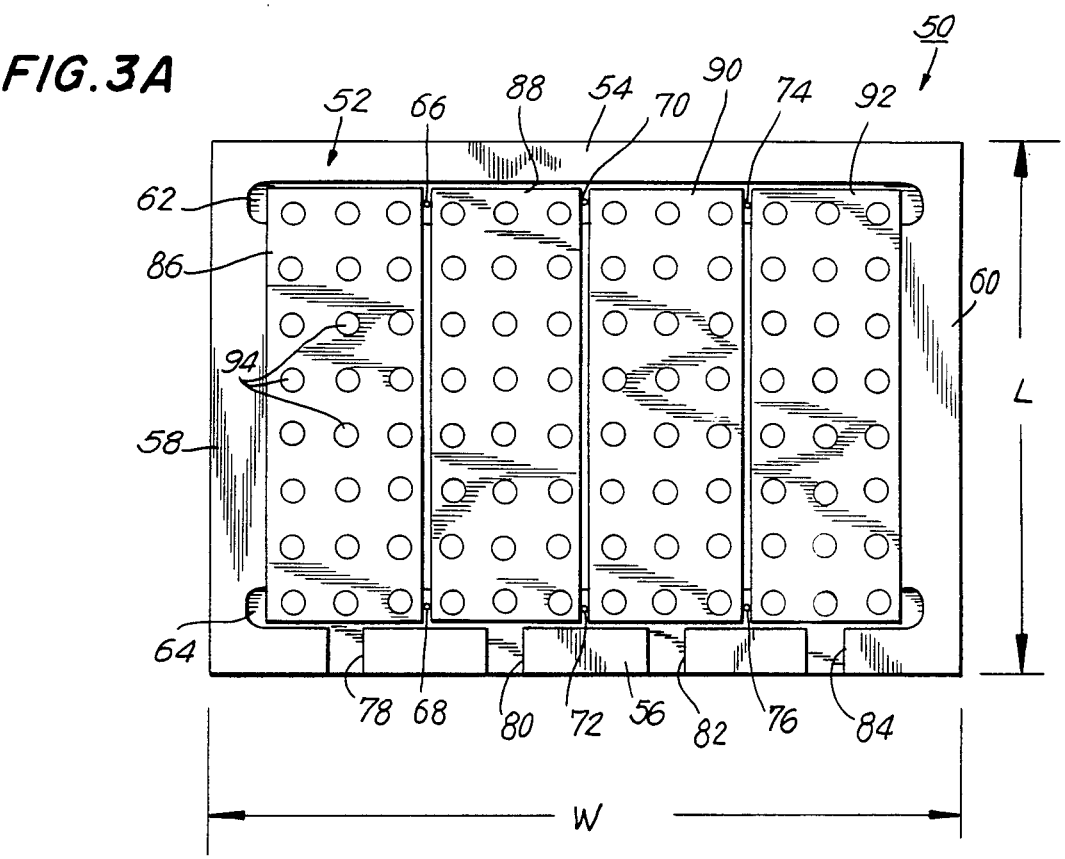
FIGS. 3A and 3B are top views representing side-by-side comparisons of the present invention and the conventional microtitration plate.
Figure 4:
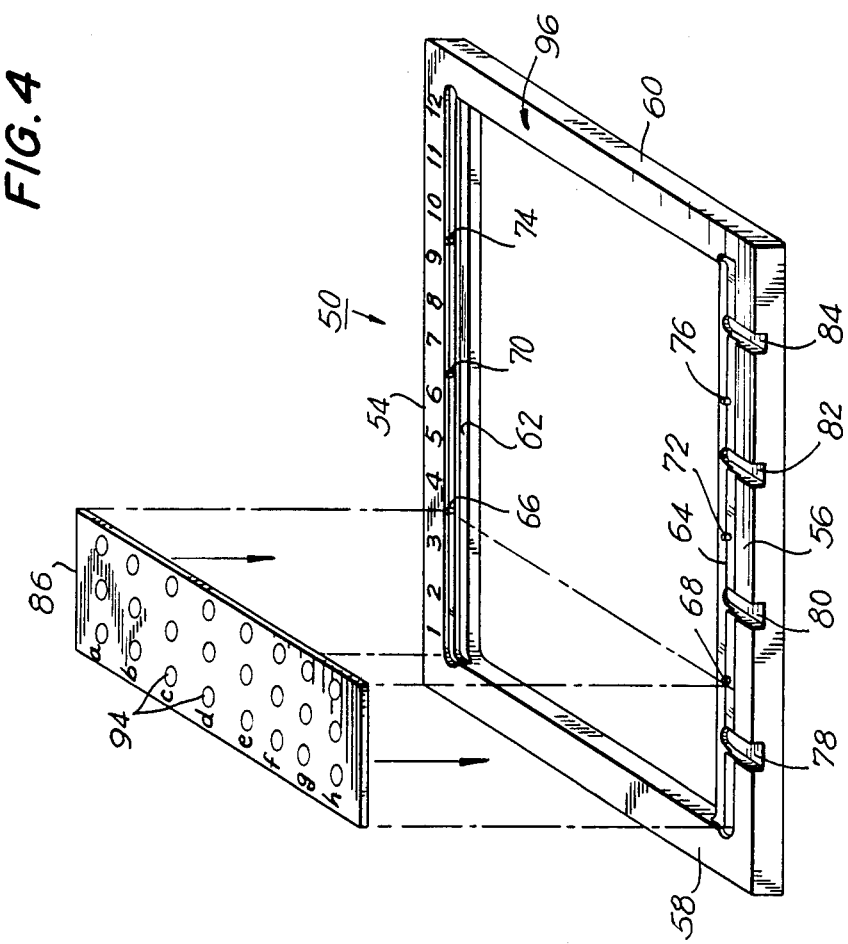
FIG. 4 is a perspective view of one embodiment of the present invention.

One embodiment of the present invention is illustrated in FIGS. 3A and 4. FIG. 3A is a top plan view of this embodiment and FIG. 4 is a perspective view thereof. This embodiment is comprised of a base 50 formed as a frame 52 and frame portions designated top portion 54, bottom portion 56, left portion 58 and right portion 60, as viewed in the drawings. The frame may be formed of plastic, metal, or the like, and is of suitable rigidity and strength to support plural tiles and to cooperate with conventional microtitration plate supports. As best seen in FIG. 4, a pair of support ledges 62 and 64 extend toward the interior of frame 52 from top and bottom frame portions 54 and 56, respectively. Alternatively, a support ledge may extend inwardly from each respective portion (i.e. from the top, bottom, left and right portions) of frame 52. However, it will be seen, from the ensuing discussion, that only a pair of support ledges are needed for the successful implementation of the present invention.

Frame 52 exhibits a length l and a width w substantially equal to length l and width w of microtitration plate 40 (FIG. 2). Frame 52 also exhibits a height h which is seen to be substantially equal to the height h of the conventional microtitration plate. The thickness, or height, of each support ledge 62 and 64 is less than height h and, thus, each support ledge is seen to be depressed below upper (or top) surface 96 of frame 52. That is, the support ledges are recessed with respect to the top surface of the frame. Preferably, but not necessarily, guide elements are provided for a purpose soon to be explained. In FIGS. 3A and 4, these guide elements are illustrated as being disposed in pairs comprised of guide elements 66, 68, guide elements 70, 72 and guide elements 74, 76. The illustrated guide elements are formed as projections which extend upwardly from support ledges 62 and 64.

Base 50 is used to support a plurality of tiles 86, 88, 90 and 92 in the embodiment illustrated in FIGS. 3A and 4. Each tile, such as tile 86, is formed as a relatively thin flat sheet constructed of glass, plastic, quartz, or the like. The thickness of the tile is approximately equal to the amount by which support ledges 62 and 64 are depressed below top surface 96 of frame 52. Each tile is formed with an array of retaining elements 94 matching the positions of the microtitration plate wells, the retaining elements preferably being constructed as relatively thin flat dishes in the tile.

As illustrated, each tile is of a length such that the opposite edges thereof are supported on support ledges 62 and 64, respectively. The pairs of guide elements 66, 68; 70, 72; and 74, 76 are seen to separate adjacent tiles. More particularly, guide elements 66, 68 separate tiles 86 and 88; guide elements 70, 72 separate tiles 88 and 90; and guide elements 74, 76 separate tiles 90 and 92. It will be appreciated, therefore, that the guide elements serve to properly position (or guide) each of tiles 86, 88, 90 and 92 in the base or frame 52.

Tile 86 (as well as tiles 88, 90 and 92) is provided with a 3×8 array of retaining elements 94. When four tiles 86, 88, 90 and 92 are supported by frame 52, the resultant array of retaining elements is seen to be an 8×12 array substantially similar to the 8×12 array of microwells 46 of the conventional microtitration plate 40 shown in FIG. 2.

One portion of frame 52, such as bottom portion 56 thereof, is provided with cut outs 78, 80, 82 and 84, these cut outs serving as finger slots, each cut out being generally centrally aligned with a respective one of tiles 86, 88, 90 and 92. These cut outs are seen to be recesses in bottom portion 56 of frame 52 and are adapted to receive a user's finger which, when inserted into a respective cut out is disposed adjacent a supported tile. This facilitates the removal of that tile from frame 52. In one embodiment, the depth of each cut out is greater than the thickness of a tile, whereupon at least the end portion of the user's finger may be inserted beneath the tile to permit easy removal thereof when the user moves his finger in the upward direction. In this manner, a tile may be easily removed from frame 52 to permit replacement thereof by a fresh tile.

Each of retaining elements 94, that is, each of the thin flat dishes, is circular and, preferably, exhibits a diameter of 3 mm. As a result, each retaining element, or dish, requires a relatively small amount of liquid sample, for example, on the order of 5–10 $\mu$l. It is seen that this quantity of liquid sample is significantly less than the 100–200 $\mu$l volumes heretofore required by microwells 46 of the conventional microtitration plate (FIG. 2). As a result, there is a substantial saving in the amount of liquid sample that must be prepared or that is available for use with the tile of the present invention.

In one embodiment, one (or both) surface of each tile may be coated with a relatively permanent, water-repellant material with the retaining elements being maintained substantially free of that water-repellant material. In this manner, localized reactions may take place within small drops of reaction liquids in the retaining elements, that is, on the surfaces of the thin flat dishes. Of course, the particular type of localized reaction that takes place is dependent upon the entity being analyzed and the type of analysis that is performed. Examples of such analyses include the determination of protein concentration, the detection of antigens or antibodies by immunoenzymatic procedures, and the like.

In another embodiment, selected biological substances, such as proteins, may be anchored permanently to selected ones (or all) of the thin flat dishes provided in a particular tile. For example, a biotin bridge may be formed between that protein and the surface of the dish or retaining element.

Reactive biological substances may be temporarily anchored to a thin flat dish by coating the clean surface of that dish with a permanent, microscopically thin film of material (such as silicon dioxide, or the like) which serves to non-permanently anchor a desired biological substance thereto. This biological substance preferably is dry and remains dry until it is released from its temporary anchorage by the addition thereto of a liquid sample or reagent. This temporary anchoring of dry substances to the tile permits such substances to be safely stored until release due to activation arising out of the addition thereto of a water-containing liquid sample.

In the embodiment shown in FIGS. 3A and 4, the central portion of frame 52 may be completely cut out, thus adding to the ease of removal of tiles 86, 88, 90 and 92 merely by pushing upwardly against those holders from below the frame. Alternatively, a solid lower surface of frame 52 may remain, this lower surface preventing the inadvertent loss of a tile that may be carelessly or errantly disposed in the frame. While such a lower surface prevents inadvertent damage to the tiles, it reduces the ease by which a tile may be removed from the illustrated base.

It will be appreciated that, in the embodiment illustrated in FIGS. 3A and 4, it is anticipated that four separate tiles will be supported on frame 52. However, it should be recognized that a greater or lesser number of such tiles may be supported by ledges 62 and 64 of frame 52. Furthermore, although not shown herein, a central rib may be disposed within frame 52 extending from left portion 58 to right portion 60, this central rib being depressed below top surface 96 by substantially the same amount as support ledges 62 and 64, and this central rib serving substantially the same purpose as the support ledges. In such a modification, it will be seen that a tile may be of approximately half the overall length of tile 86, such a shortened tile being supported between the aforementioned central rib and one of support ledges 62 and 64. Thus, rather than utilizing four separate tiles, eight such reduced size tiles may be employed, each being individually removable from frame 52. Each such tile thus may be provided with a 3×4 array (as opposed to the illustrated 3×8 array) of retaining elements, thereby adding to the flexibility of use of the illustrated apparatus. That is, rather than substitute a 3×8 tile for separate analyzing runs, all that may be necessary is the substitution of a smaller 3×4 tile if a smaller number of samples is to be analyzed.

Figure 3B:
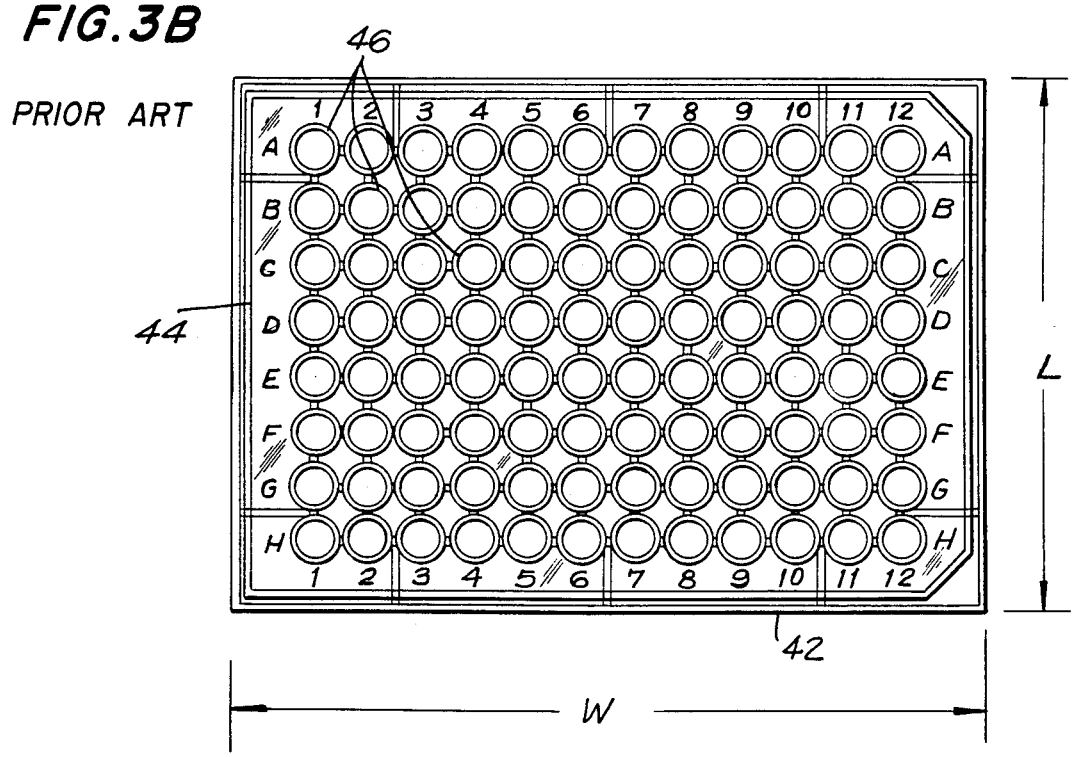

A side-by-side comparison of the present invention with a conventional microtitration plate is illustrated by the juxtaposed devices shown in FIGS. 3A and 3B. It is seen that the overall dimensions l, w and h of both devices are the same; and that retaining elements 94 provided on tiles 86, 88, 90 and 92 occupy substantially the same positions as microwells 46. Thus, the conventional reading and liquid-sample loading apparatus normally used with conventional microtitration plates may be used with the base and tiles of the present invention. That is, base 50 is seen to be compatible with existing, conventional microtitration plate support apparatus.

Although separate tiles 86, 88, 90 and 92 are preferred, it will be appreciated that frame 52 may be used with a single tile having, for example, an 8×12 array of retaining elements. That is, a single tile may be used in place of the four individual tiles that comprise the microcircle system illustrated in FIG. 3A.

Also, although a plurality of cut outs 78, 80, 82 and 84 are illustrated in FIGS. 3A and 4, it will be appreciated that, if desired, only a single such cut out may be present. If four tiles are supported at one time by frame 52, it will be recognized that the removal of one facilitates the easy removal of the remaining three. Consequently, only one cut out need be provided as a finger slot to facilitate the removal of that first tile.

Although cut outs 78, 80, 82 and 84 have been described above as extending to a depth beneath support ledge 64, it is appreciated that, if desired, such cut outs may extend merely to support ledge 64. Also, although each cut out is seen to be generally centered with respect to a respective tile, the particular positioning of the cut out may vary, as desired. Such central disposition is not necessary to the successful practice of the present invention.

Figure 5:
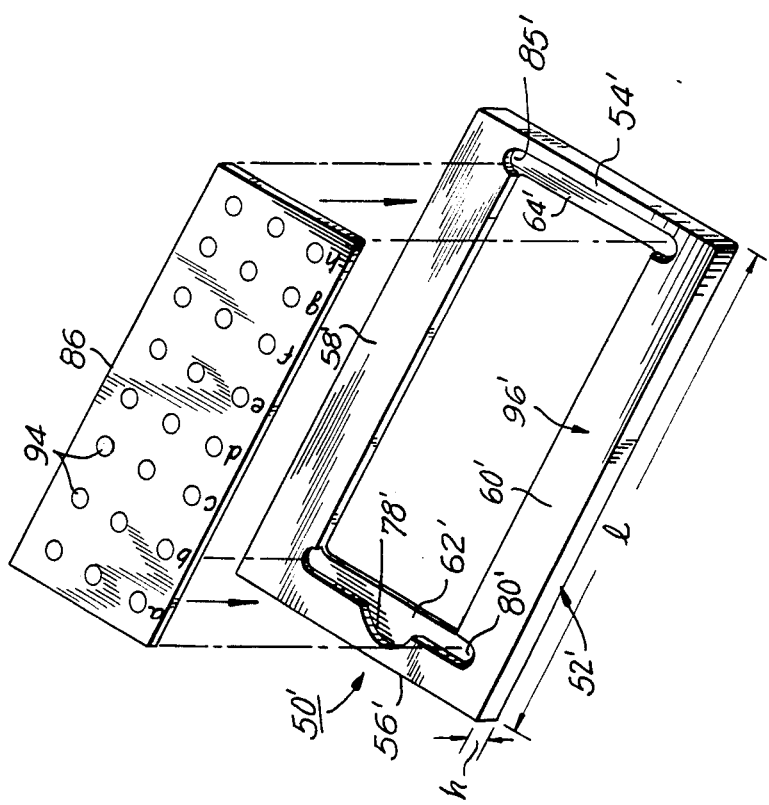
FIG. 5 is a perspective view of another embodiment of the present invention.

An alternative embodiment of the present invention is illustrated in FIG. 5. This embodiment differs from that described above in conjunction with FIGS. 3A and 4 in that base 50' of the FIG. 5 embodiment is adapted to support only a single tile 86 rather than the plural tiles discussed above. A plurality of such bases 50', each supporting a respective tile, may be positioned side-by-side in a conventional microtitration plate support in place of the conventional microtitration plate 40. For ease of appreciating the embodiment shown in FIG. 5, the same reference numerals have been used (with primes) as have been used previously to identify similar parts. In the interest of brevity, a further detailed but duplicative discussion of the embodiment shown in FIG. 5 need not be provided.

As before, cut out 78' is disposed in bottom portion 56' of frame 52'. In addition to cut out 78', additional cut outs 80', 82' and 84', 85' may be provided in the vicinity of the respective corners of tile 86 when the latter is supported on support ledges 62' and 64'.

If desired, a central rib, similar to the aforementioned central rib that may be added to the embodiment shown in FIGS. 3A and 4, may extend between left portion 58' and right portion 60' to carry out the same function as support ledges 62' and 64'. With this central rib, tile 86 may be formed as two separate tiles, each of approximately half the size of the illustrated tile. It is appreciated that each such tile of reduced size is supported between the aforementioned central rib and a respective one of support ledges 62' and 64'.

The corner cut outs 80', 82', 84' and 85', although not necessary, are useful in facilitating the removal of a tile from frame 52'. If desired, such corner cut outs may be omitted.

Figure 6A:
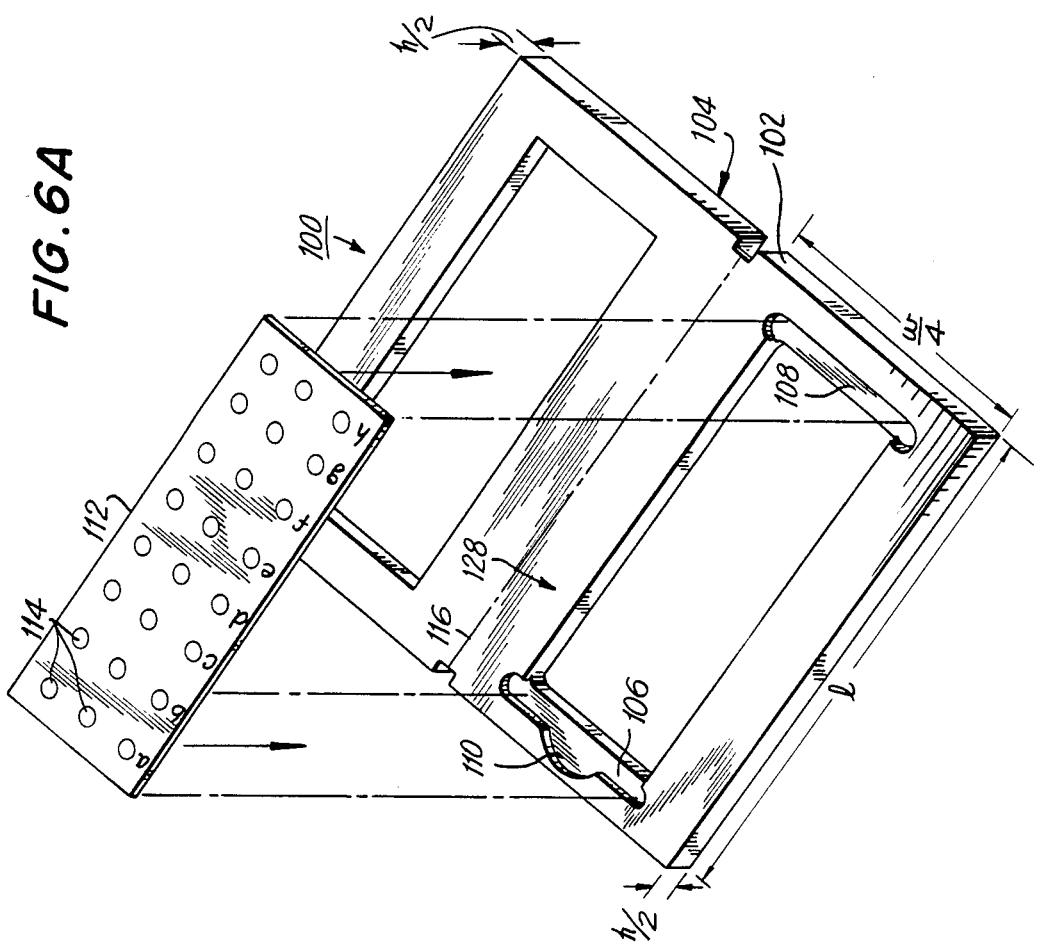
FIGS. 6A–6C are perspective views of yet another embodiment of the present invention.
Figure 6C:
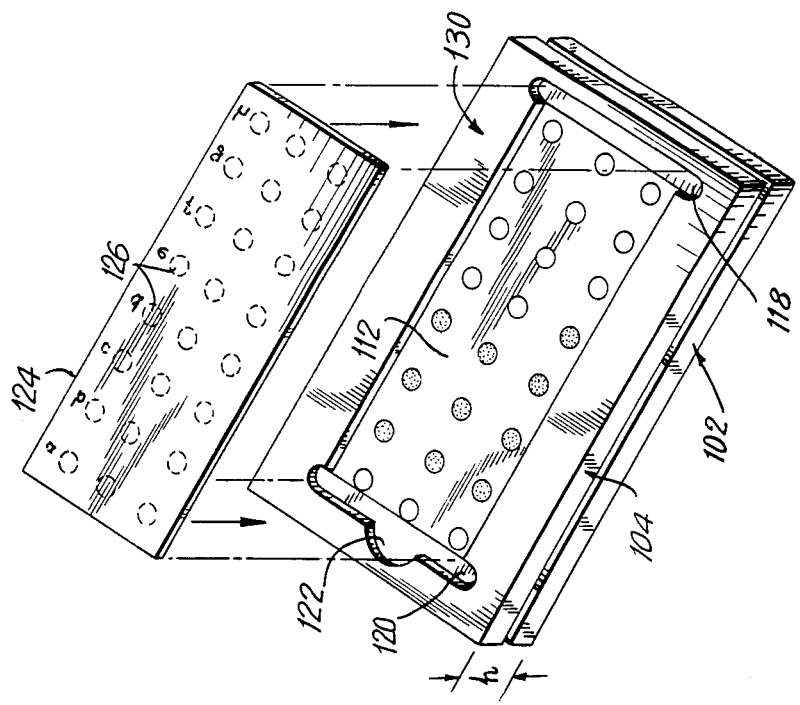
Figure 6B:
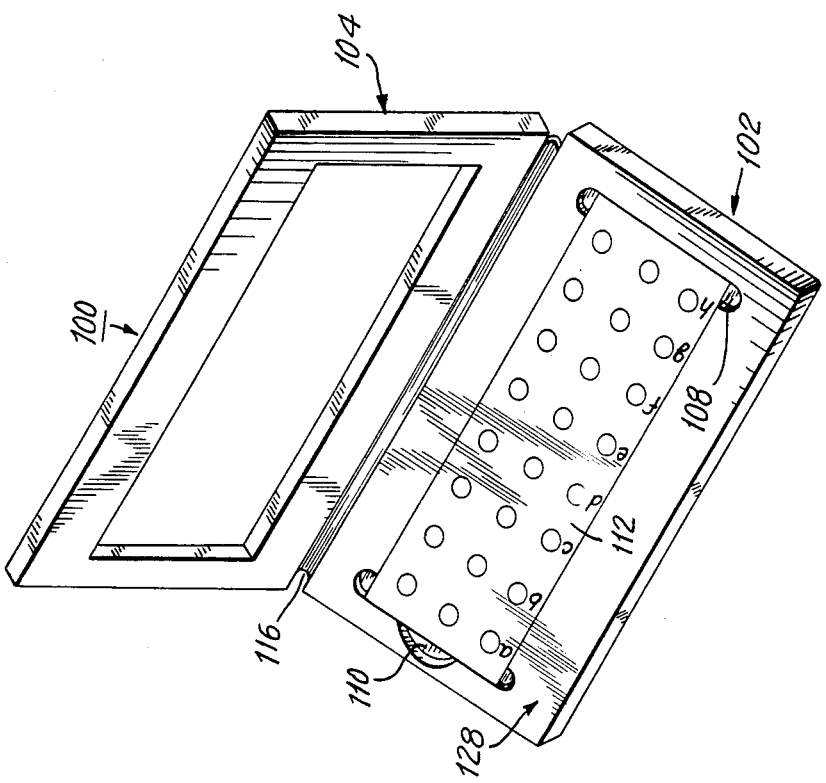

Yet another embodiment of the present invention is illustrated in FIGS. 6A-6C. This embodiment is comprised of a base 100 formed of two separate frame sections 102 and 104, each section being referred to herein simply as a frame. Frames 102 and 104 are of substantially identical construction and dimensions, and it is seen that one relatively long side of frame 102 is hingedly connected to a similarly long side of frame 104 by means of a hinge 116. This hinge may be formed of thin flexible plastic material or other means by which the two frames may be hingedly connected to each other. Hinge 116 serves as a pivot axis about which either or both frames are rotatable between an open position, as illustrated in FIG. 6A, to a closed position, as illustrated in FIG. 6C. When in this closed position, it is appreciated that frame 104 is disposed atop frame 102.

When frames 102 and 104 are disposed in the closed position illustrated in FIG. 6C, that is, when frame 104 is disposed atop frame 102, the height h of the combined frames is seen to be equal to the height h of the conventional microtitration plate 40 (FIG. 2). Preferably, although not necessarily, each frame 102 and 104 may exhibit a height that is substantially equal to h/2.

Each of frames 102 and 104 may be of substantially the same configuration as frame 52' shown in FIG. 5. As an example, the length of each frame l preferably is substantially equal to the length l of the conventional microtitration plate. The width of each frame may be approximately equal to a submultiple of the width of the conventional microtitration plate. For example, if the width of each frame is approximately equal to w/4, four closed frames (as shown in FIG. 6C) may be disposed side-by-side in the conventional microtitration plate support. Of course, the left and right portions 58' and 60' of each frame will be quite thin in order to approximate the width w/4.

Each of frames 102 and 104 is designed to receive and support a respective tile. In this regard, frame 102 is provided with a pair of oppositely disposed support ledges 106 and 108 which, as illustrated, and consistent with the foregoing embodiments, extend inwardly from opposite sides of the frame. The height of each support ledge 106, 108 is seen to be less than the height of frame 102 and, thus, these support ledges are depressed below top surface 128 of this frame. A cut out 110, similar to aforedescribed cut outs 78, 80, 82 and 84, is disposed in top surface 128 at, for example, the bottom portion of the frame. Cut out 110 is seen to extend downwardly to support ledge 106 and is designed to receive the user's finger which, when positioned adjacent tile 112, permits the removal of that tile from frame 102. As illustrated, the tile is provided with retaining elements 114 similar to aforedescribed retaining elements 94.

After tile 112 is positioned within frame 102, frame 104 may be pivoted about hinge 116, as shown in FIG. 6B, to the closed position illustrated in FIG. 6C. It is seen that frame 104 is provided with support ledges 118 and 120, similar to aforementioned support ledges 106 and 108. Frame 104 also is provided with a cut out 122 that is similar to aforementioned cut out 110.

Tile 124 is designed to be positioned within frame 104 and supported by oppositely located support ledges 118 and 120. Tile 124 may be substantially identical to aforementioned tile 112 and, when these tiles are supported in their respective frames, retaining elements 114 of one tile are aligned with retaining elements 126 of the other. Furthermore, when the respective tiles are supported on their respective support ledges, the tiles are spaced apart by a distance such that a liquid sample that may be contained on one of retaining elements 114 contacts an aligned one of retaining elements 126 so as to form a liquid bridge therebetween.

It is seen, from FIGS. 6A-6C, that when frames 102 and 104 are disposed in their open position (FIG. 6A), top surface 128 of frame 102 and top surface 130 of frame 104 face in opposite directions. Furthermore, tile 112 may be disposed in frame 102 when the frames are in their open position; and tile 124 may be disposed in frame 104 when the frames are in their closed position.

When using the embodiment shown in FIGS. 6A-6C, liquid samples may be added to desired retaining elements 114 of tile 112 after frames 102 and 104 are pivoted to their closed position, but before tile 124 is disposed in frame 104. Then, tile 124 is disposed in frame 104 such that the aligned retaining elements of both tiles exhibit a face-to-face relationship. As a result, the liquid samples located on the lower tile 112 contact the thin flat dishes of the aligned retaining elements 126 of the upper tile 124, thereby forming a liquid bridge, or stable column, of liquid sample between the aligned, opposing dishes. A chemical or other reaction occurring in this bridge may be measured with conventional instruments.

It will be appreciated that the tiles shown and described in each of the embodiments herein may be of substantially the same construction having similar coatings thereon. As mentioned above, reagents may be permanently anchored to all or selected ones of the retaining dishes. Alternatively, reactive biological substances may be temporarily anchored, or attached, to these dishes such that the reactive biological substances remain dry until activated by the addition thereto of water-containing samples or other liquids. In the embodiment shown in FIGS. 6A-6C, the reactive biological substances may be anchored to lower tile 112 and such adherence to upper tile 124 may be avoided by creating a "non-stick" barrier between the dried biological substances and the surfaces of the retaining dishes of the upper tile.

Figure 7:
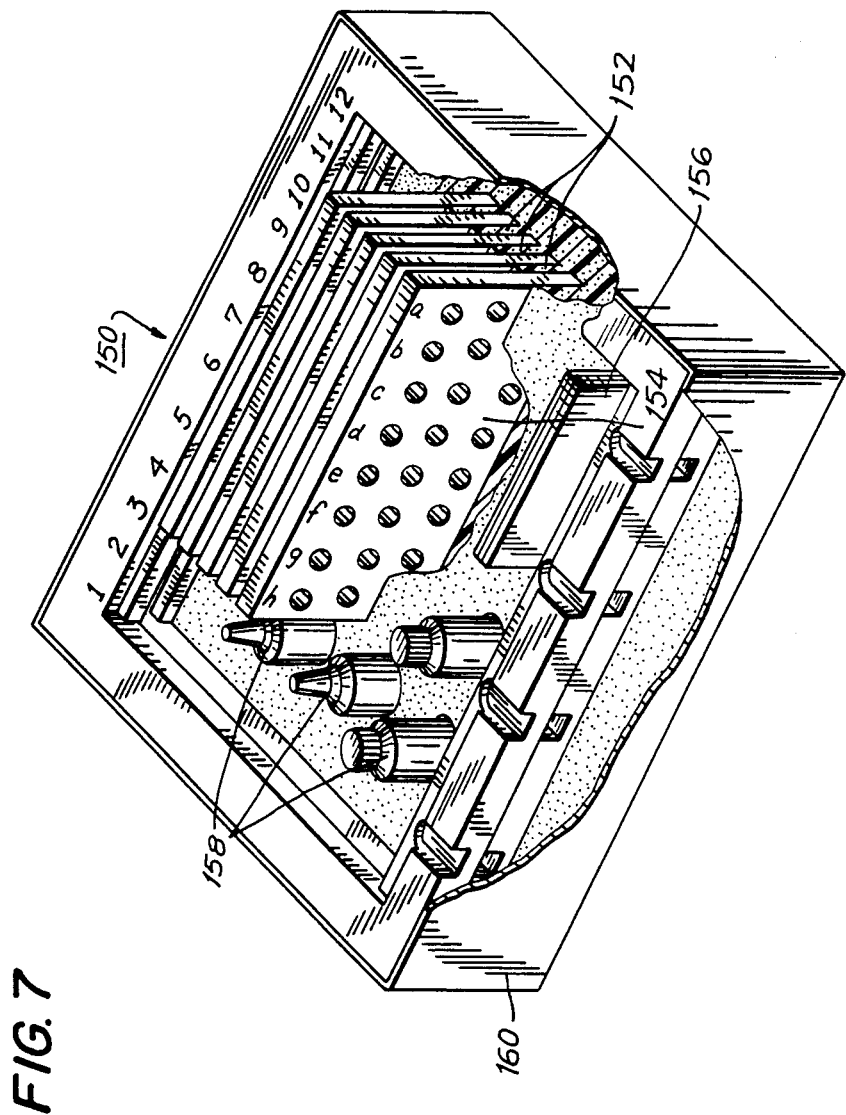
FIG. 7 represents a kit containing portions of the present invention.

It will be appreciated from the foregoing discussion that the embodiments illustrated herein are designed for use in a conventional microtitration plate support in place of the conventional microtitration plate. By reason of the easy removal and substitution of relatively small tiles, the same apparatus that heretofore has been used with, for example, an 8×12 array of microwells may be used with the present invention while permitting quick and easy substitution of tiles. For example, if less than all of the retaining elements of one tile are used for one run, it is not necessary to replace the entire base for another run using different liquid samples. Rather, it merely is sufficient to add additional tiles or to replace a fresh tile for a used one in order to carry out succeeding runs. Furthermore, by using relatively thin flat dishes in place of deeper microwells, the test washing procedure performed on the tiles used in the present invention is much simpler and quicker than the cleansing operation heretofore needed for conventional microtitration plates. Other advantages of the present invention have been discussed above and still further advantages will be readily appreciated by those of ordinary skill in the art. For example, the combination of base and tiles may be packaged, together with containers of various reagents, in a "kit". This kit 150, shown in FIG. 7, is readily used for assays and may include a support rack 152 for supporting a number of tiles 154 and an instruction booklet 156 to advise users of the particular reagents 158 that may be used for different assays or analyses, and the manner in which those reagents should be applied to the retaining elements, or dishes, of each tile. The rack, tiles, booklet and reagents may be housed in container 160. A micropipette also may be included for purposes of reagent application.

While the present invention has been particularly shown and described with reference to certain preferred embodiments, it will be appreciated by those of ordinary skill in the art that various changes and modifications may be made without departing from the spirit and scope of the invention. It is intended that the appended claims be interpreted as including such changes and modifications as well as equivalents to the present invention.

What is claimed is:

1. Apparatus for use in a conventional microtitration plate support in place of a microtitration plate that has a plurality of microwells, said apparatus comprising a generally rectangular base including a frame having a plural sides, the frame being of height h substantially equal to the height of said conventional microtitration plate, length l substantially equal to the length of said conventional microtitration plate, and width w substantially no greater than the width of said conventional microtitration plate; a pair of support ledges extending toward the interior of said frame from opposite sides of said frame; and at least one tile formed as a thin sheet of material having an array of thin, flat retaining dishes for retaining drops of liquid samples, said tile having edge portions supportable on said pair of support ledges of said frame.

2. The apparatus of claim 1 wherein a plurality of substantially identical tiles have edge portions supportable on said support ledges of said frame.

3. The apparatus of claim 1 wherein said frame has an upper surface and said support ledges are recessed from said upper surface.

4. The apparatus of claim 3 wherein said upper surface is provided with at least one finger slot disposed in a side of the frame for enabling a user's finger to be inserted adjacent a supported tile and thereby facilitate removal of said tile from said base.

5. The apparatus of claim 4 wherein the number of finger slots disposed in said side of the frame is equal to the number of tiles supportable therein.

6. The apparatus of claim 1 wherein said frame comprises first and second frame sections disposable one atop the other, the total height of said first and second frame sections when so disposed being substantially equal to h.

7. The apparatus of claim 6 wherein at least one tile is supportable in each of said first and second frame sections.

8. The apparatus of claim 7 wherein said first and second frame sections are substantially identical to each other and are dimensioned such that when they are disposed one atop the other, the tile supported in one is spaced from the tile supported in the other with the retaining dishes of the respective tiles being in alignment.

9. The apparatus of claim 8 wherein a liquid bridge formed of a drop of liquid sample is suspended between two aligned retaining dishes of said spaced tiles.

10. The apparatus of claim 6 further comprising hinge means for connecting said first and second frame sections to each other, whereby said frame sections are pivotable about said hinge means into position such that one frame section is disposed atop the other.

11. The apparatus of claim 1 further comprising guide means for defining respective guide positions for plural tiles supported on said support ledges of said frame.

12. The apparatus of claim 11 wherein said guide means comprise a pair of upstanding guide elements, each guide element extending upwardly from a respective ledge, to separate adjacent tiles.

13. Apparatus for use in a conventional microtitration plate support in place of a microtitration plate that has a plurality of microwells, said apparatus comprising a generally rectangular base including a frame having a plurality of sides, the frame being of height h substantially equal to the height of said conventional microtitration plate, length l substantially equal to the length of said conventional microtitration plate, and width w substantially no greater than the width of said conventional microtitration plate; a pair of support ledges extending toward the interior of said frame from opposite sides of said frame; and at least one tile formed as a thin sheet of material having an array of retaining elements for retaining drops of liquid samples, said tile having edge portions supportable on said pair of support ledges of said frame; said at least one tile comprising a thin, flat sheet of material, and an array of thin, flat dishes formed in said tile, each dish having a diameter on the order of 3 mm.

14. The apparatus of claim 13 further comprising a water-repellant coating on a surface of said tile, with said array of thin, flat dishes being free of said water-repellant coating.

15. The apparatus of claim 13, further comprising a reagent for reacting with a drop of liquid sample when the latter is applied to at least one of said dishes; and means for anchoring said reagent to said dish in advance of the application of said liquid sample thereto.

16. The apparatus of claim 15 wherein said reagent is dry and said means for anchoring comprises material for temporarily anchoring the dry reagent to said dish until a water-containing liquid sample is applied thereto.

17. Apparatus for use in a conventional microtitration plate support in place of a microtitration plate of the type having a plurality of microwells, said apparatus comprising a generally rectangular frame of height h substantially equal to the height of said conventional microtitration plate, length l substantially equal to the length of said conventional microtitration plate, and width w substantially equal to the width of said conventional microtitration plate; at least one pair of support ledges provided on said frame and extending interiorly thereof, said support ledges being of lesser dimension than said height h and being depressed below the top surface of said frame; tile means comprised of a sheet of material having an array of thin, flat dishes formed in said tile means for retaining drops of liquid sample, said tile means bieng disposable on and supportable by said pair of ledges; and means provided along a side of said frame to receive a use's finger, a portion of said finger when inserted into said means passing adjacent said tile means to facilitate the removal of said tile means from said frame.

18. The apparatus of claim 17 wherein said tile means comprises a single tile having the same number and location of dishes formed therein as the number and location of microwells normally provided on said conventional microtitration plate.

19. The apparatus of claim 17 wherein said tile means comprises plural tiles having edge portions supportable on said ledges, the tiles being disposed in side-by-side relationship.

20. The apparatus of claim 19 wherein said means to receive a user's finger comprises plural finger slots, each disposed in alignment with a respective tile supported in said frame such that, when a user's finger is inserted therein, the aligned tile is removable from said frame.

21. The apparatus of claim 19 further comprising separating means disposed on said ledges for separating adjacent tiles and for positioning said tiles in said frame.

22. The apparatus of claim 21 wherein said separating means comprise at least one pair of projections extending upwardly from said ledges, each projection in a pair being provided on a respective one of said ledges.

23. Apparatus designed to be used in a conventional microtitration plate support in place of a microtitration plate of the type having a plurality of microwells, said apparatus comprising a generally rectangular frame of height h substantially equal to the height of said conventional microtitration plate, length l substantially equal to the length of said conventional microtitration plate, and width w substantially equal to a submultiple of the width of said conventional microtitration plate; a pair of support ledges provided on said frame and extending interiorly thereof, the height of said support ledges being less than h and said support ledges being recessed from the top surface of said frame; a tile disposable on and supportable by said pair of ledges, said tile having an array of thin flat dishes formed therein equal in number to a submultiple of the number of microwells normally provided in said conventional microtitration plate for retaining drops of liquid sample; and at least one cut out provided in the top surface of said frame to receive a user's finger which, when inserted therein, guides a portion of said finger adjacent said tile to facilitate the removal of said tile from said frame.

24. The apparatus of claim 23 wherein said cut out extends downward to one of said ledges and is generally centered with respect to a tile supported in said frame.

25. The apparatus of claim 23 wherein plural cut outs extend downward to one of said ledges and are located at the vicinity of the corners of a tile supported in said frame.

26. The apparatus of claim 25 wherein a respective cut out is located at the vicinity of each corner of a tile supported in said frame.

27. Apparatus designed to be used in a conventional microtitration plate support in place of a microtitration plate of the type having a plurality of microwells, said apparatus comprising two generally rectangular frames disposable one atop the other and having a total height h when so disposed that is substantially equal to the height of said conventional microtitration plate, each frame having length l substantially equal to the length of said conventional microtitration plate and width w substantially equal to a submultiple of the width of said conventional microtitration plate; each frame including a pair of support ledges provided thereon and extending interiorly thereof, the height of said support ledges being less than the height of the respective frame and said support ledges being recessed from the top surface of said respective frame; a respective tile supportable by each frame, said tile being disposable on and supportable by a respective pair of ledges and positioned to face the tile supported by the other frame, each tile having an array of thin flat dishes formed therein equal in number to a submultiple of the number of microwells normally provided in said microtitration plate for retaining drops of liquid sample; and at least one cut out provided in the top surface of each frame to receive a user's finger which facilitates the removal of said tile from said frame.

28. The apparatus of claim 27 wherein said two frames are hingedly interconnected along a respective side thereof and movable between a closed position in which the frames are disposed one atop the other, and an open position in which the frame are disposed side by side to each other.

29. The apparatus of claim 28 wherein the top surfaces of said two frames face in opposite directions when said frames are in said open position.

30. The apparatus of claim 29 wherein one tile is positionable in one frame when said frames are in said open position, and another tile is positionable in the other frame when said frames are in said closed position.

31. An assay kit, comprising: a generally rectangular base including a frame of height and length substantially equal to the height and length, respectively, of a conventional microtitration plate, and of width substantially no greater than the width of said conventional microtitration plate; a pair of support ledges extending toward the interior of said frame from opposite sides thereof; plural tiles, each formed as a thin sheet of material having an array of thin, flat retaining dishes for retaining drops of liquid samples, at least one of said tiles being supportable on said pair of support ledges of said frame; plural containers of reagents for respectively different analyses of samples, each reagent being useable to be applied to at least some of the retaining dishes of a tile; and packaging means for housing at least said tiles and said plural containers of reagents.

* * * * *

UNITED STATES PATENT AND TRADEMARK OFFICE
CERTIFICATE OF CORRECTION

PATENT NO. : 4,682,891

DATED : July 28, 1987

INVENTOR(S) : Everly Conway de Macario et al.

It is certified that error appears in the above-identified patent and that said Letters Patent is hereby corrected as shown below:

On the title page: Items [19] and [75],
Correct the last name of the first-named inventor to read as follows: --Conway de Macario--.

In the Abstract, at line 4, after "height" correct the spelling of "and".

Claim 17, column 13, line 14, correct the spelling of "being".

Claim 28, column 14, line 41, change "frame" to --frames--.

Signed and Sealed this

Twenty-fourth Day of November, 1987

Attest:

DONALD J. QUIGG

*Attesting Officer*  *Commissioner of Patents and Trademarks*